United States Patent [19]
Jessie et al.

[11] Patent Number: 6,129,051
[45] Date of Patent: Oct. 10, 2000

[54] COLLAPSIBLE INSECT CONTAINER

[75] Inventors: Donald K. Jessie, Aurora; David C. Bergman, Batavia, both of Ill.

[73] Assignee: Processed Plastic Company, Montgomery, Ill.

[21] Appl. No.: 09/145,355

[22] Filed: Sep. 1, 1998

[51] Int. Cl.[7] .......................... A01K 1/03; A01K 31/06; A01K 97/00; A01K 97/04; B65D 25/00
[52] U.S. Cl. .......................... 119/452; 119/474; 43/54.1; 43/55; 220/9.4
[58] Field of Search .............................. 43/1, 4, 55, 54.1, 43/121, 118, 122; 119/452, 474, 223; 220/9.4, 676; D22/136

[56] References Cited

U.S. PATENT DOCUMENTS

| | | | |
|---|---|---|---|
| 269,625 | 12/1882 | Blake | 248/98 |
| 955,027 | 4/1910 | Weigland | 220/9.4 |
| 1,052,379 | 2/1913 | Ranken | 220/9.4 |
| 1,643,407 | 9/1927 | Florance | 220/9.1 |
| 1,936,644 | 11/1933 | Schoder | 43/121 |
| 2,538,853 | 1/1951 | Worl | 43/55 |
| 2,575,893 | 11/1951 | Seaman | 43/55 |
| 2,620,588 | 12/1952 | Critser | 43/55 |
| 2,739,410 | 3/1956 | Budnick | 43/55 |
| 2,756,912 | 7/1956 | Armstorng | 224/5 |
| 2,767,757 | 10/1956 | Marder | 220/9.4 |
| 3,141,257 | 7/1964 | Stull | 43/55 |
| 3,272,376 | 9/1966 | Tierney et al. | 220/19 |
| 3,308,570 | 3/1967 | Horton | 43/55 |
| 3,908,704 | 9/1975 | Clement et al. | 138/21 |
| 4,030,226 | 6/1977 | Shelton, Sr. et al. | 43/55 |
| 4,158,267 | 6/1979 | Farnsworth | 43/55 |
| 4,354,543 | 10/1982 | Bogner | 220/9.4 |
| 4,441,272 | 4/1984 | Bartz | 43/1 |
| 4,890,413 | 1/1990 | Nelson et al. | 43/55 |
| 5,243,781 | 9/1993 | Carter | 43/122 |
| 5,478,152 | 12/1995 | Bogle | 220/9.4 |
| 5,544,781 | 8/1996 | Mattesky | 220/9.4 |
| 5,622,277 | 4/1997 | Van Giezen et al. | 220/9.4 |
| 5,671,858 | 9/1997 | Hsu | 220/9.4 |
| 5,702,001 | 12/1997 | Russell et al. | 206/388 |

FOREIGN PATENT DOCUMENTS

| | | | |
|---|---|---|---|
| 85194 | 3/1895 | Germany | 119/452 |
| 2532342 | 2/1977 | Germany | 119/452 |
| 63768 | 4/1913 | Switzerland | 119/452 |
| 6345 | 1/1889 | United Kingdom | 43/55 |

OTHER PUBLICATIONS

"The Evening Star" Washington, D.C., Things for Boys to Make, T.W. Burgess, Jan. 1922.

*Primary Examiner*—Michael J. Carone
*Assistant Examiner*—Fredrick T. French, III
*Attorney, Agent, or Firm*—Keith B. Willhelm

[57] ABSTRACT

A collapsible insect containers are provide that comprise a base, a top having a selectively closeable passageway therein, at least one support member that extends between and engages the base and top and supports the top in spaced relation to the base, and pliant sidewalls that extend between the base and top and enclose the space therebetween. By utilizing pliant sidewalls, the container, absent support by the support members, is collapsible and may be packaged in a collapsed state.

20 Claims, 2 Drawing Sheets

COLLAPSIBLE INSECT CONTAINER

BACKGROUND OF THE INVENTION

The present invention relates to an insect container and, more particularly, to a collapsible, toy insect container that is suitable for collection and display of insects.

Children enjoy catching and watching insects, and there are a number of prior art devices that have been used for such purposes. Perhaps the most common device is simply a glass jar with a suitably perforated metal lid. The large opening allows the insects to be easily placed in the jar, and the glass walls provide clear visibility for viewing captive insects. The hazards associated with broken glass and the sharp points of perforations in the lid, however, have led to efforts to develop containers for the collection and display of insects that are safer for children to use.

An example of one such device is shown in U.S. Pat. No. 3,272,376 to J. Tierney et al. The insect container disclosed therein utilizes generally rigid screen mesh for the container walls. The bottom end of the generally tubular shaped screen mesh is potted into a cup shaped base with casting plaster. The upper end is covered with a folded cloth strip and resiliently engages a lid.

This container has significant safety advantages over the use of glass jars. At the same time, however, it is relatively expensive to make, as are other such devices that employ relatively rigid screen. Relatively costly measures must be taken to secure the mesh to the base and top of the container, such as the potting process disclosed in the aforementioned Tierney '376 patent. Alternately, the screen may be welded or soldered, but such processes also are relatively expensive.

Perhaps more significantly, however, is that the use of relatively rigid screen results in a relatively bulky product. Thus, the cost of shipping such products is increased, and the products will occupy more space on warehouse and retail shelves. Such manufacturing and distribution costs are particularly critical when the container is designed to be a toy as such items can be extremely price sensitive.

Finally, it is well known that toys frequently are packaged and sold in a disassembled state, in substantial part because of the cost of distributing large, bulky products. At the same time, however, the assembly of toys is a source of constant complaints from parents who generally must shoulder that task for their children.

An object of this invention, therefore, is to provide insect containers that are easily and safely handled by a child, that securely entrap insects, and that allow for excellent observation of captive insects.

It also is an object to provide such containers that are more economically manufactured.

Another object of this invention is to provide such insect containers that are more economically shipped, stored and displayed.

Yet another object is to provide such containers that may be packaged and shipped in a substantially complete state requiring a little or no further assembly by a consumer.

It is a further object of this invention to provide such insect containers wherein all of the above-mentioned advantages are realized.

Those and other objects and advantages of the invention will be apparent to those skilled in the art upon reading the following detailed description and upon reference to the drawings.

SUMMARY OF THE INVENTION

The subject invention provides for insect containers comprising a base, a top having a selectively closeable passageway therein, at least one support member that extends between and engages said base and top and supports said top in spaced relation to the base, and pliant sidewalls that extend between the base and top and enclose the space therebetween. It will be appreciated, therefore, that by utilizing pliant sidewalls the container, but for the support provided by support members, is collapsible. Thus, for example, it may be packaged, shipped, and sold in a nearly complete state of assembly. The only assembly required by a consumer is insertion of support members. Yet, because the container is collapsible before insertion of the support members, packaging for the container is more compact, and the product is more economically shipped, stored and retailed.

Alternate embodiments of the invention have a collapsible support member that provides the necessary support for the container while it is in use. The container may be packaged in a completely assembled state, and because the container has pliant sidewalls it may be collapsed for more compact packaging.

The containers of the subject invention preferably comprise substantially tubular pliant sidewalls having a lower end attached to a base ring that is engaged with the base. The sidewalls have an open upper end that is attached to a top ring that is engaged with the top. As will become apparent from the discussion which follows, such rings and the overall simplicity of the design provide for containers that are easily and economically fabricated, and that also allow for easy collection and observation of insects.

DESCRIPTION OF ILLUSTRATIVE EMBODIMENTS

Figure 1:
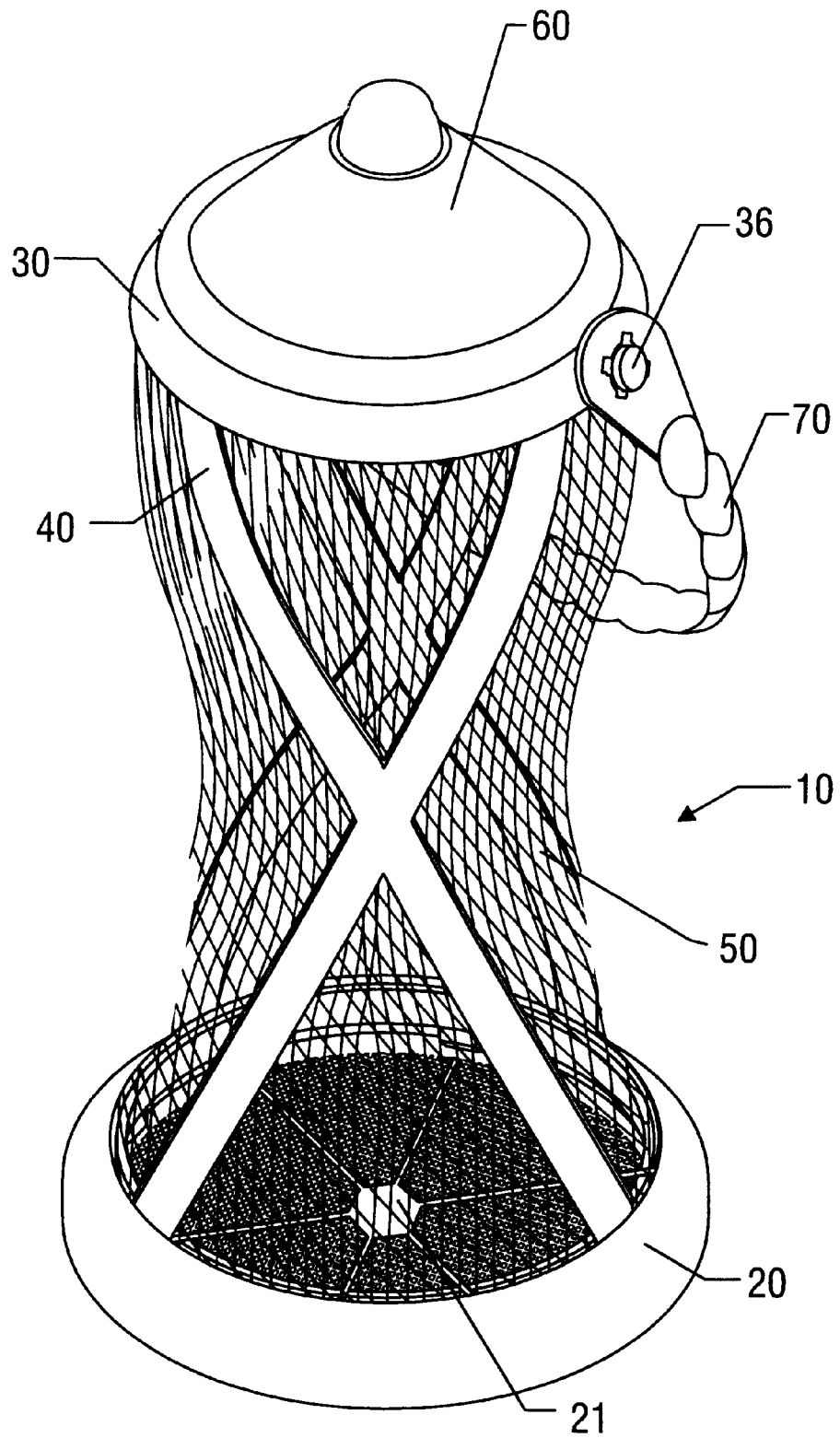
FIG. 1 is a perspective view of a preferred embodiment of the insect containers of the subject invention showing an insect container 10 in its completely assembled state.
Figure 2:
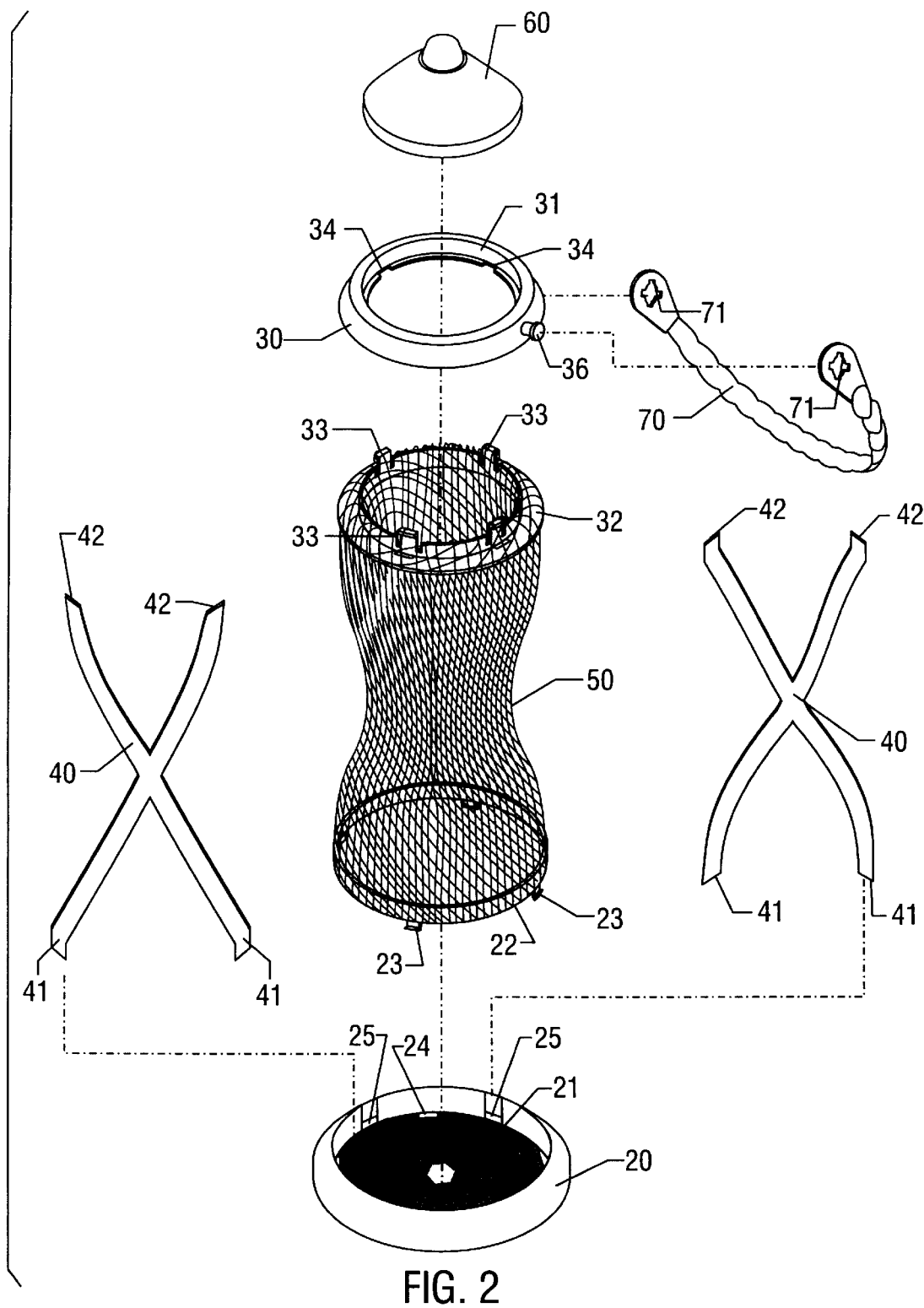
FIG. 2 is an exploded, perspective view of the insect container 10 shown in FIG. 1 showing the various components of the container 10.

The containers of the subject invention, such as the preferred embodiment 10 illustrated in FIGS. 1–2, comprise pliant sidewalls. As seen in FIG. 1, the container 10 generally comprises a base 20 and a top 30. A pair of support arms 40 extend between and engage the base 20 and the top 30 and support the top 30 in spaced relation to the base 20. A generally tubular netting 50 extends between the base 20 and the top 30 and encloses the space between the base 20 and top 30. The netting 50 thereby defines pliant sidewalls of the container 10.

The pliant sidewalls of the novel containers may be fabricated from any material that allows for sufficiently unobstructed observation of insects, while preventing their escape from the container. Importantly, the material is sufficiently pliant that, in the absence of support members, it will allow the container to collapse, thereby allowing the container to be packaged in a more compact fashion, all of which will be explained in further detail below.

Thus, the netting 50 is constructed of any suitable woven or nonwoven, synthetic or natural fiber fabric mesh or the like. In lieu of netting, sheer fabric may be used. Clear, pliant plastic films and the like also may be used. Other such pliant materials are known and may be used.

The top of the novel insect containers has a selectively closeable passageway to allow insects to be placed in the container and to prevent their escape therefrom. For example, as seen by comparing FIG. 1 and FIG. 2, the top 30 of container 10 has a passageway 31. The passageway 31 is sufficiently large to accommodate the passage of insects into said container. A lid 60 is provided to cover the passageway 31 once insects have been placed in the container 10. The lid is configured to frictionally engage the passageway 31, thereby preventing the accidental uncovering of the passageway 31.

It will be appreciated, however, that while the frictionally engageable lid 60 is preferred because it provides excellent performance while being easily and economically manufactured, other designs are known and may be used if desired. For example, container tops may be provided with lids that screw into or snap over the passageway. A sliding or rotating cover also may be used. The specific design of the selectively closeable passageway in the top of the novel containers forms no part of the subject invention.

Preferably, the containers of the subject invention are provided with some means for carrying them. For example, container 10 is provided with a bail handle 70 which is secured through openings 71 to posts 36 on top 30. Other handles and the like, however, may be used, and many suitable designs are known to those skilled in the art.

As seen best in FIG. 2, the base 20 has a perforated floor 21. It is not necessary for the floor to be perforated, but the perforations do allow additional air circulation through the container and for that reason are preferred.

The bottom end of the netting 50 is secured to a base ring 22 by folding it over the ring 22 and by stitching the hem formed thereby. As best appreciated from FIG. 2, the base ring 22 in turn is attached to the base 20 by a set of four projections 23 that engage a set of four openings 24 in the base 20. Likewise, the open top end of the netting 50 is secured to a top ring 32 that is attached to the top 30 by a set of projections 33 that engage portions 34 of an annular rim in opening 31 in the top 30. The projections 23 and 33 preferably are designed to snap into the openings 24 and over the rim portions 34.

As will be readily appreciated, the netting 50 may be easily, securely and economically attached to the rings 22 and 32 and thereby to the base 20 and top 30. As best seen in FIG. 1, this design provides a neat, seamless appearance to the container 10, and for those reasons it is preferred. In other embodiments, however, the pliant sidewalls may be secured directly to the base and top, and they may be secured by adhesives or other means. Likewise, if rings are used, they may be attached to the base and top by other means, such as by adhesives. In its broadest aspects, the subject invention contemplates the use of any suitable means of securing the pliant sidewalls to the base and top and a variety of suitable means are known and within the skill of the art.

Likewise, it will be noted that the rings 22 and 32 are generally circular. Nevertheless, and normal connotations notwithstanding, the "rings" of the subject invention may have other configurations, such as rectangular, when a generally rectangular or other shape is desired for the novel containers.

The insect containers of the subject invention comprise at least one support member extending between and engaging the base and top. The support members support the top in spaced relation to the base. For example, in the preferred embodiment 10, there are two support arms 40, each having a generally X-shaped configuration. The lower ends 41 of the support arms 40 engage a corresponding set of four openings 25 in the base 20 of the container 10. Similarly, the upper ends 42 of the support arms 40 engage a corresponding set of four openings (not shown) in the top 30. Preferably, the ends 41 and 42 of the support arms 40 are adapted, to snap into the openings 25 in base 20 and the openings in the top 30, respectively, or to be frictionally engaged therein.

The support arms 40 of container 10 are preferred because they may be easily and reliably assembled by a consumer. A variety of other support members and arms are known and may be used, however, so long as they provide the necessary structural support and do not significantly interfere with viewing of captive insects. Likewise, other means of engaging the support arms to the base and top of the container are known by those skilled in the art and may be used. For example, the support arms may be secured thereto by screws, plastic rivets or the like.

It will be appreciated, therefore, that in the absence of support members, the containers of the subject invention are collapsible, the pliant sidewalls allowing the base and top to collapse upon themselves to provide for a more compact subassembly. The collapsed subassembly, along with the support members, will fit into a much smaller package that the completely assembled container.

It will further be appreciated that the overall design of the containers of the subject invention is simple and readily susceptible to being economically fabricated. The majority of the components of the novel containers may be fabricated, for example, from polypropylene by well known injection molding techniques. Once fabricated, especially when the parts are designed to snap-in or frictionally engage, the containers are easily assembled.

Importantly, however, it will be appreciated that shipping and other distribution costs can be minimized at the same time that the product is shipped in a nearly complete state of assembly. That is, preferably the containers are packaged as a subassembly that includes the base, top, and pliant sidewalls, with the support arms to be assembled by the consumer.

For example, in respect to the container 10, the netting 50 is secured to the base ring 22 and top ring 32, and the rings 22 and 32 are engaged, respectively, to the base 20 and top 30, all as described above. This subassembly, along with the support arms 40, then is packaged, with final assembly of the support arms 40 to the subassembly to be done by the consumer.

Assembly by the consumer, therefore, is kept to a minimum. At the same time, the novel containers may be more compactly packaged in this manner than if they were packaged in their fully assembled state. Since the packaged containers will occupy less space in shipping containers and on stockroom and display shelves, there will be corresponding savings in shipping and distribution costs.

Alternatively, by using a collapsible support member, the novel containers may be shipped in a fully assembled condition. For example, a resilient member, such as a spring, may be used to support and spread the container top and bottom. In such an embodiment, the spring would be compressed for packaging, and the resiliency of the spring would enable it to support the container when it is in use. Similarly, corrugated snap tubing may be used as support members. Such tubing can be collapsed for packaging the container and extended for use. Such corrugated snap tubing is known in the art, e.g., as disclosed in U.S. Pat. No. 3,908,704 to I. Clement et al and U.S. Pat. No. 3,409,224 to H. Harp et al. Other collapsible supports, such as articulated arms, are known in the art and may be used.

While this invention has been disclosed and discussed primarily in terms of specific embodiments thereof, it is not intended to be limited thereto. Other modifications and embodiments will be apparent to the worker in the art.

What is claimed is:

1. A container for collecting and viewing insects comprising:
   (a) a base;
   (b) a top having a selectively closeable passageway therein that is adapted to accommodate the passage of insects and to prevent the egress of insects from said container;
   (c) at least one support member extending between and engaging said base and top and supporting said top in spaced relation to said base; and
   (d) pliant sidewalls extending continuously between said base and top and enclosing the space therebetween to prevent the egress of insects from therein while allowing viewing of insects in said container, said pliant sidewalls further allowing said base and top to collapse upon themselves in the absence of support provided by said support member.

2. The insect container of claim 1, wherein said pliant sidewalls comprise a fabric mesh.

3. The insect container of claim 1, wherein said top has a lid adapted to cover said passageway in said top to prevent the egress of insects from said container.

4. The insect container of claim 1, wherein said base comprises a perforated floor.

5. The insect container of claim 1, wherein said support member is collapsible.

6. A container for collecting and viewing insects comprising:
   (a) a base;
   (b) a base ring engaging said base;
   (c) a top having a selectively closeable passageway to accommodate the passage of insects into said container and to prevent the egress of insects from said container;
   (d) a top ring engaging said top;
   (e) at least one support member extending between said base and top and supporting said top in spaced relation to said base; and
   (f) pliant sidewalls allowing viewing of insects in said container and extending continuously between said base and top and enclosing the space therebetween so as to prevent the egress of insects from therein; said pliant sidewalls having a lower end attached to said base ring and an open upper end attached to said top ring, said pliant sidewalls further allowing said base and said top to collapse upon themselves in the absence of support provided by said support member.

7. The insect container of claim 6, wherein said pliant sidewalls comprise a fabric mesh.

8. The container of claim 6, wherein said base comprises a perforated floor.

9. The container of claim 6, wherein said base ring has projections engaging openings in said base and securing said base ring to said base.

10. The container of claim 6, wherein said top has a lid adapted to cover said passageway in said top to prevent the egress of insects from said container.

11. The container of claim 6, wherein said top ring has projections engaging an annular rim projecting into said passageway in said top.

12. The container of claim 6, wherein said container comprises support arms, the lower ends of said support arms engaging a set of openings in said base and upper ends of said support arms engaging openings in said top.

13. A container for collecting and viewing insects comprising:
   (a) a subassembly comprising a base; a base ring engaging said base; a top having a selectively closeable passageway to accommodate the passage of insects into said container and to prevent the egress of insects from said container; a top ring engaging said top; and pliant sidewalls extending continuously between said base and top and enclosing the space therebetween to prevent the mess of insects from therein while allowing viewing of insects in said container, said pliant sidewalls having a lower end attached to said base ring and an open upper end attached to said top ring; and
   (b) support arms extending between said base and top and supporting said top in spaced relation to said base, said support arms being adapted to engage said subassembly;
   (c) wherein said container may be packaged for shipping and display with said support arms disengaged from said subassembly and with said subassembly in a collapsed condition such that final assembly of said container is performed by a consumer thereof by engaging said support arms to said subassembly.

14. The insect container of claim 13, wherein said pliant sidewalls comprise a fabric mesh.

15. The container of claim 13, wherein said base comprises a perforated floor.

16. The container of claim 13, wherein said base ring has projections engaging openings in said base and securing said base ring to said base.

17. The container of claim 13, wherein said top has a lid adapted to cover said passageway in said top to prevent the egress of insects from said container.

18. The container of claim 13, wherein said top ring has projections engaging an annular rim projecting into said passageway in said top.

19. The container of claim 13, wherein lower ends of said support arms engage a set of openings in said base and upper ends of said support arms engage openings in said top.

20. A container for collecting and viewing insects comprising:
   (a) a base having a perforated floor and first and second sets of openings;
   (b) a base ring having a set of projections engaging said first set of openings in said base and securing said base ring to said base;
   (c) a top having a passageway adapted to allow ingress of insects into said container, an annular rim projecting into said passageway, and a set of openings;
   (d) a top ring having a set of projections engaging said annular rim in said passageway of said top and securing said top ring to said top;
   (e) a lid adapted to cover said passageway in said top to prevent the egress of insects from said container;
   (f) support arms extending between said base and top and supporting said top in spaced relation to said base, said support arms having lower ends engaging said second set of openings in said base and upper ends engaging said set of openings in said top; and
   (g) a tubular, pliant netting extending between said base and top and enclosing the space therebetween; said netting having a lower end attached to said base ring and an open upper end attached to said top ring.

* * * * *

UNITED STATES PATENT AND TRADEMARK OFFICE
CERTIFICATE OF CORRECTION

PATENT NO : 6,129,051
DATED : October 10, 2000
INVENTOR(S) : Donald K. Jessie and David C. Bergman It is certified that error appears in the above-identified patent and that said Letters Patent is hereby corrected as shown below:

In claim 13, at column 6, line 10, delete "mess", and insert therein -- egress --.

Signed and Sealed this

Eighth Day of May, 2001

*Attest:*

NICHOLAS P. GODICI

*Attesting Officer*          Acting Director of the United States Patent and Trademark Office